United States Patent [19]

Ashton et al.

[11] Patent Number: 4,745,235

[45] Date of Patent: May 17, 1988

[54] ORGANIC FLUORIDES FROM FLUOROFORMIC ESTERS

[75] Inventors: David P. Ashton, Warrington; Thomas A. Ryan, Kelsall; Brett A. Wolfindale, Liverpool, all of United Kingdom

[73] Assignee: Imperial Chemical Industries PLC, London, England

[21] Appl. No.: 96,785

[22] Filed: Sep. 14, 1987

Related U.S. Application Data

[63] Continuation of Ser. No. 778,300, Sep. 23, 1985, abandoned, which is a continuation of Ser. No. 582,232, Feb. 21, 1984, abandoned.

[30] Foreign Application Priority Data

Mar. 1, 1983 [GB] United Kingdom ................ 8305593

May 26, 1983 [GB] United Kingdom ................ 8314561

[51] Int. Cl.$^4$ ..................... C07C 17/00; C07C 17/33; C07C 25/02
[52] U.S. Cl. .................................... 570/142; 558/282
[58] Field of Search .......................................... 570/142

[56] References Cited

U.S. PATENT DOCUMENTS 3,283,018 11/1966 Christe et al. ....................... 570/142

Primary Examiner—J. E. Evans
Attorney, Agent, or Firm—Cushman, Darby & Cushman

[57] ABSTRACT

A method for the preparation of an organic fluoride by contacting a fluoroformic acid ester with alumina at a temperature in the range 200°–600° C.

6 Claims, No Drawings

ORGANIC FLUORIDES FROM FLUOROFORMIC ESTERS

This is a continuation of application Ser. No. 778,300, filed Sept. 23, 1985, now abandoned, which is a continuation of Ser. No. 582,232, filed Feb. 21, 1984, now abandoned.

This invention relates to a chemical process and more particularly to a method for the preparation of organic fluorides.

The preparation of fluorobenzene by the thermal decomposition of phenyl fluoroformate has been described by K O Christe and A E Pavlath (J. Org. Chem., 30, 3170, 1965) who passed gaseous phenyl fluoroformate through a hot tube containing various catalysts. The best results were obtained with platinum gauze as a filling material using temperatures in the range 600°–850° C.

The same process is described by the same authors in U.S. Pat. No. 3,283,018. Temperatures of 350°–900° C. are mentioned, the preferred range being 600°–850° C. when platinum gauze is used as catalyst.

It has now been found that by employing a catalyst comprising alumina, the decarboxylation reaction proceeds faster and at much lower temperatures than has previously been reported.

Thus, according to the invention, there is provided a method for the preparation of an organic fluoride which comprises contacting a fluoroformic acid ester with alumina at a temperature in the range 200°–600° C.

Fluoroformic acid esters which may be used in accordance with the invention have the formula:

ROCOF wherein R represents an optionally substituted hydrocarbyl or heterocyclic radical. Substituents which may be present in the said radicals include halogen atoms, for example chlorine and fluorine atoms, and fluoroformic ester groups. In the latter case, starting with a material containing two or more fluoroformic ester groups, the product will be the corresponding di- or higher fluoride.

Hydrocarbyl radicals which may be represented by R include alkyl, alkenyl, cycloalkyl, cycloalkenyl, aralkyl, aralkenyl and aryl radicals.

Since some fluoroformates, for example alkyl fluoroformates, decarboxylate readily under relatively mild conditions, the method of the invention is especially suitable for the more thermally stable fluoroformates which normally require more drastic conditions for decarboxylation. Accordingly, preferred starting materials are optionally substituted aryl fluoroformates, for example phenyl fluoroformate, 4-chlorophenyl fluoroformate and 2,4,6-trimethylphenyl fluoroformate, and enol fluoroformates of the formula:

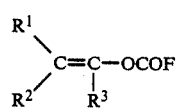

wherein each of $R^1$, $R^2$ and $R^3$, independently, is hydrogen or an optionally substituted hydrocarbyl radical or $R^2$ and $R^3$ together form a hydrocarbon chain containing three or four carbon atoms. Examples of enol fluoroformates which may be used include vinyl fluoroformate, isopropenyl fluoroformate, 1-tertbutylvinyl fluoroformate, 1-cyclopropylvinyl fluoroformate, 1-phenylvinyl fluoro-formate and 1-cyclohexenyl fluoroformate.

The fluoroformates may be obtained by known methods, for example, by reaction between a chloroformate and an inorganic fluoride, for example fluorspar. Aryl fluoroformates may also be obtained by reacting the appropriate phenol with carbonyl chlorofluoride.

The alumina used in the method of the invention preferably has a surface area of at least 10 $m^2/g$, gamma-alumina being particularly suitable. The performance of the alumina may be enhanced by the deposition thereon of a Group VIII metal, especially a platinum group metal, for example palladium, rhodium or preferably, platinum itself. The metals may be deposited on the alumina as salts or complexes followed by reduction. Silica, titania and carbon shown no catalytic activity.

Excellent yields of fluoride have been obtained at reaction temperatures not exceeding 300° C. but higher temperatures up to 600° C. may be employed if desired. The production of unwanted by-products due to hydrolysis of the fluoroformate may be minimised by operating under substantially anhydrous conditions. Atmospheric, superatmospheric or subatmospheric pressures may be employed.

The organic fluoride may be isolated from the reaction product in conventional manner.

The invention is illustrated but not limited by the following Examples:

EXAMPLE 1

A catalyst was prepared by the impregnation of gamma-$Al_2O_3$ with 10% w/w of $H_2[PtCl_6]$ followed by drying in nitrogen and reduction with hydrogen at 450° C. The catalyst was finally purged with a further amount of nitrogen, again at 450° C. The surface area of the prepared catalyst was measured to be 167 $m^2/g$ and the Pt content was 4.8% by weight.

This catalyst was tested in a stainless steel microreactor tube sited on top of a Hewlett-Packard 5790 gas chromatograph and attached directly onto the injection port in place of the septum cap holder. The reactor, heated by an aluminium alloy block furnace, was capped by a second injection port. Both of the injection ports were heated to about 300° C. and separate streams of helium were fed into each port, one at the reactor inlet and the other at the outlet.

Liquid phenyl fluoroformate (1 ul) was injected into the inlet helium stream (controlled at a flow rate of 10 ml/min) and the vapourised material permitted to pass through the catalyst plug (0.1–0.25 ml) following which the product gases were further diluted with the second helium stream (50 ml/min) before being analysed by gas chromatography (3 m, 6 mm OD column containing 20% SP 2100 and 0.1% Carbowax 1500 on Supelcoport; 200° C. isothermal; FID). The high dilution was necessary in order to avoid the condensation of any high-boiling organic products, such as diphenyl carbonate, particularly in view of the high operating pressure of 2.6 bar.

The results of the screening of this catalyst are recorded in the following Table. Fluorobenzene was the major product obtained over the whole of the temperature range examined (255°–465° C.). Initially, a yield of 72.2% of fluorobenzene was obtained at 465° C. which settled to about 55% at a later stage in the temperature scan. A small amount of benzene was also generated initially which diminished as the surface hydride (presumably formed during the reduction stage) was depleted. Diphenyl carbonate was produced only when the temperature was below 350° C. reaching a maximum yield of about 25% at 287° C.

For the purpose of comparison, the reaction was also carried out using, firstly, platinum gauze and, then, platinum black as catalyst.

Using platinum gauze over the temperature range of 252°–468° C., only trace quantities of fluorobenzene were produced, the major reaction product being diphenyl carbonate. Platinum black (surface area 24 $m^2/g$) was more active than the platinum gauze and showed consistently higher conversions of the phenyl fluoroformate feed. However, the principal reaction product was diphenyl carbonate, not fluorobenzene.

The results obtained using these catalysts are given in the following Table.

| Catalyst | Temp- erature (°C.) | Con- tact Time (s) | Con- version (%) | Yields (%) $C_6H_5F$ | $(C_6H_5)_2CO_3$ |
|---|---|---|---|---|---|
| 4.8% $Pt/Al_2O_3$ | 218 | 0.36 | 56.9 | 21.4 | |
| (0.098 g, 0.1 ml) | 255 | 0.33 | 99.1 | 53.9 | 9.5 |
| | 351 | 0.29 | 99.9 | 56.8 | 0 |
| | 399 | 0.27 | 99.9 | 59.8 | 0 |
| | 313 | 0.31 | 99.8 | 57.9 | 17.3 |
| | 287 | 0.32 | 92.3 | 55.3 | 25.4 |
| | 464 | 0.23 | 99.7 | 59.8 | 0 |
| Pt gauze | 468 | 0.31 | 43.3 | 0 | 37.5 |
| (2.87 g, 0.13 ml) | 350 | 0.38 | 19.6 | 0 | 11.4 |
| | 305 | 0.41 | 23.1 | 0.15 | 10.8 |
| | 411 | 0.35 | 31.3 | 0.19 | 20.7 |
| | 252 | 0.44 | 22.6 | 0.09 | 3.7 |
| Pt black | 467 | 0.25 | 96.0 | 0.13 | 86.4 |
| (0.075 g, 0.11 ml) | 372 | 0.30 | 34.7 | 0.11 | 36.2 |
| | 304 | 0.34 | 15.9 | 0.13 | 15.2 |
| | 250 | 0.36 | 8.9 | 0.13 | 8.7 |
| | 427 | 0.28 | 86.2 | 0.19 | 77.9 |
| | 459 | 0.27 | 96.4 | 0.85 | 85.7 |

On the basis of these results it is estimated that the activity of the platinum/alumina catalyst, measured at 255° C., is about 1000 times greater than the platinum gauze catalyst, operated at 800° C., described by Christe and Pavlath. At comparable temperatures (255° C.) our measurements show that the platinum gauze material gives an activity of $2.5 \times 10^{-3}$ gramme of fluorobenzene per gramme of platinum per hour compared to an activity of about 1,240 gramme of fluorobenzene per gramme of platinum per hour for the platinum on alumina catalyst: the production rate having therefore increased by a factor of half a million.

In a further experiment, the catalyst used was gamma-$Al_2O_3$ (not impregnated by $H_2[PtCl_6]$). The results were substantially the same as those given by the platinum/alumina catalyst.

EXAMPLE 2

Carbonyl chlorofluoride was passed into a dry toluene solution of 2,4,6-trimethylphenol at 60° C. to give 2,4,6-trimethylphenyl fluoroformate in 96% yield based on the trimethylphenol charged. The product was identified by NMR and mass spectroscopy.

The 2,4,6-trimethylphenyl fluoroformate in the form of a toluene solution was converted to 1-fluoro-2,4,6-trimethylbenzene using the catalyst, apparatus and procedure described in paragraphs 1, 2 and 3 of Example 1. At a temperature of 350° C., a 61% yield of the fluoro compound was obtained based on the fluoroformate charged. The 1-fluoro-2,4,6-trimethylbenzene was identified by both NMR and mass spectroscopy.

EXAMPLE 3

Carbonyl chlorofluoride was passed into a dry solution of 4-chlorophenol (1 g) and triethylamine (50 μl) in toluene (15 g) at 60° C. to give 4-chlorophenyl fluoroformate (99.8% yield) which was identified by both NMR and mass spectroscopy.

The 4-chlorophenyl fluoroformate in the form of a toluene solution was contacted with γ-alumina (Harshaw Al 3912 P) having a surface area of 166 $m^2/g$ using the apparatus and procedure described in paragraphs 2 and 3 of Example 1. At a temperature of 500° C., a 14.6% yield of 1-chloro-4-fluorobenzene (identified by mass spectroscopy) was obtained.

EXAMPLE 4

Phenyl fluoroformate was contacted with several potential catalysts under the conditions already described. The optimum fluorobenzene yields and associated temperatures are recorded below:

| Catalyst | Surface Area ($m^2/g$) | Optimum Yield (%) | Temp (°C.) |
|---|---|---|---|
| γ-$Al_2O_3$ | 188 | 66 | 340 |
| 2.1% Pd/γ-$Al_2O_3$ | 166 | 53 | 325 |
| 2.1% Rh/γ-$Al_2O_3$ | 166 | 49 | 300 |
| γ-$Al_2O_3$ | 166 | 48 | 300 |
| η-$Al_2O_3$ | 100 | 36 | 310 |
| $SiO_2$ | 350 | 0 | 450 |

EXAMPLE 5

Using the apparatus described in Example 1, vinyl fluoroformate vapour diluted with nitrogen (total volume 1 ml) was injected into the helium stream (50 ml/min) at the microreactor inlet and the vapor permitted to flow through the catalyst plug (0.01 ml) held at the required temperature.

An optimum vinyl fluoride yield of 35% at 250° C. was observed using a 4% Pt/γ-$Al_2O_3$ catalyst of surface area 167 $m^2/g$. The vinyl fluoride was identified by gas chromatography-mass spectroscopy.

We claim:
1. A method for the preparation of an organic fluoride of the formula RF where R is phenyl, 4-chlorophenyl or 2,4,6-trimethylphenyl which comprises contacting a fluoroformic acid ester of the formula ROCOF with alumina at a temperature in the range 200°–600° C.

2. A method according to claim 1 wherein the ester is phenyl fluoroformate or 2,4,6-trimethylphenyl fluoroformate.

3. A method according to claim 1 wherein the alumina has a surface area of at least 10 $m^2/g$.

4. A method according to claim 1 wherein the alumina is gamma-alumina.

5. A method according to claim 1 wherein the alumina has a Group VIII metal deposited thereon.

6. A method according to claim 5 wherein the Group VIII metal is a platinum group metal.

* * * * *